US009743676B2

United States Patent
O'Connor (10) Patent No.: US 9,743,676 B2
(45) Date of Patent: Aug. 29, 2017

(54) PESTICIDAL COMPOSITIONS COMPRISING A SOLID INSECTICIDE AND AN ESSENTIAL OIL

(71) Applicant: AirRx Antimicrobial Sciences Inc., Baltimore, MD (US)

(72) Inventor: Linda-Lou O'Connor, Severna Park, MD (US)

(73) Assignee: AirRx Antimicrobial Sciences Inc., Baltimore, MD (US)

( * ) Notice: Subject to any disclaimer, the term of this patent is extended or adjusted under 35 U.S.C. 154(b) by 0 days.

(21) Appl. No.: 15/142,427

(22) Filed: Apr. 29, 2016

(65) Prior Publication Data

US 2016/0316765 A1   Nov. 3, 2016

Related U.S. Application Data

(60) Provisional application No. 62/155,345, filed on Apr. 30, 2015.

(51) Int. Cl.
| | |
|---|---|
| A01N 61/02 | (2006.01) |
| A01N 65/22 | (2009.01) |
| A01N 25/06 | (2006.01) |
| A01N 43/36 | (2006.01) |
| A01N 47/40 | (2006.01) |
| A01N 61/00 | (2006.01) |
| A01N 53/00 | (2006.01) |
| A01N 43/40 | (2006.01) |

(52) U.S. Cl.
CPC ............ *A01N 65/22* (2013.01); *A01N 25/06* (2013.01); *A01N 43/36* (2013.01); *A01N 43/40* (2013.01); *A01N 47/40* (2013.01); *A01N 53/00* (2013.01); *A01N 61/00* (2013.01)

(58) Field of Classification Search
CPC ....... A01N 65/00; A01N 25/006; A01N 61/02
See application file for complete search history.

(56) References Cited

U.S. PATENT DOCUMENTS

| 4,518,593 A | 5/1985 | Juvin et al. |
| 6,231,865 B1 | 5/2001 | Hsu et al. |
| 7,534,447 B2 | 5/2009 | Bessette et al. |
| 2012/0301532 A1* | 11/2012 | Carey .................... A01N 25/08 424/411 |
| 2013/0142893 A1 | 6/2013 | Bessette et al. |
| 2014/0205547 A1 | 7/2014 | Okamoto et al. |
| 2015/0132413 A1* | 5/2015 | Bessette ................ A01N 31/04 424/745 |

FOREIGN PATENT DOCUMENTS

WO   2011/161546   12/2011

OTHER PUBLICATIONS

Borugă et al., "Thymus vulgaris essential oil: chemical composition and antimicrobial activity," *Journal of Medicine and Life* 7(3): 56-60, 2014.
Cleversley, "Essential Oils to Get Rid of Bed Bugs," retrieved from https://blog.essentialoilexchange.com/essential-oils-to-get-rid-of-bed-bugs/, posted Feb. 5, 2014, 2 pages.
Feldlaufer et al. "Essential Oils as Fumigants," *J. Entomol. Sco* 50(2): 129-137, 2015.
Potter et al. "Bed Bug Nation: Is the United States Making Any Progress?," *Proceedings of the Eighth International Conference on Urban Pests*, pp. 51-58, 2014.
Romero et al., "Evaluation of chlorfenapyr for control of the bed bug, *Cimex lectularius* L.," *Pest Manag Sci* 66: 1243-1248, 2010.
Salido et al., "Chemical Composition and Seasonal Variations of Rosemary Oil from Southern Spain," *J. Essent. Oil Res.* 15: 10-14, 2003.

* cited by examiner

*Primary Examiner* — Sudhakar Katakam
(74) *Attorney, Agent, or Firm* — Seed IP Law Group LLP (57) ABSTRACT

A liquid composition for controlling a target pest by aerosol application to a space in need thereof is disclosed. The composition comprises a solid insecticide dissolved in a solvent comprising an essential oil or oils, wherein the solid insecticide is selected from the group consisting of pyrethroid, neonicotinoid and halogenated pyrrole insecticides, and wherein the solid insecticide is present at a concentration sufficient to control the target pest. Methods for controlling a target pest by aerosol application to a space in need thereof are also disclosed, such methods comprising the step of aerosolizing the liquid composition, thereby contacting the space with an insecticidally effective amount of the liquid composition.

27 Claims, 6 Drawing Sheets

PESTICIDAL COMPOSITIONS COMPRISING A SOLID INSECTICIDE AND AN ESSENTIAL OIL

BACKGROUND

Technical Field

This invention generally relates to novel insecticidal compositions and methods for use of the same for controlling a target pest.

Description of the Related Art

General household insect pests have the potential to cause nuisance or harm to person and property. Nuisance insects can infest an individual's living environment at any place and at any time. Infestations can cause anxiety, physical ailments, and economic hardship. Although bed bugs have not been proven to transmit diseases, they are classified as a major public health problem due to their negative impact on the quality of life. Bed bugs cause a number of adverse health effects, including skin rashes, blisters, severe itching, loss of sleep, psychological effects, and allergic symptoms. Bed bug infestations can also create economic hardship, such as high treatment costs, displacement, decreased work productivity, and loss of wages. In commercial setting, such as in hotels, theaters, and residential complexes, revenue can be significantly impacted by infestations due to treatment costs and loss of services.

Various insecticide compositions have been developed to control bed bugs and other household pests. The primary objective in developing an insecticidal compound is its "knockdown" and "mortality" potential. Knockdown refers to quick, short-term, immobilization. Knockdown usually occurs within a short period of time, but is dependent on the pest. Pests can recover from knockdown immobilization depending on their tolerance for the insecticides and their recovery abilities. Mortality refers to the death of the pest.

An optimal insecticide composition would have a knockdown and mortality rate near 100% and its application method would be proficient at reaching its intended target. Over the years, widespread use of synthetic chemical insecticides has led to insecticide resistance among certain household insects. Insecticides, such as pyrethroids, carbamates, and organophosphates are not as effective as they were 15 years ago. Insecticide resistance has been postulated to be the key initiator of the resurgence in bed bugs. Contact insecticides with no residual effects, such as pyrethrum, are ineffective even when encountering a non-resistant strain if the application method fails to reach its target. Other, insecticides, such as chlorfenapyr alone, provide residual effects achieving a reduction in the pest populations only after several weeks. An insecticide composition with no known insect resistance that can be effectively delivered to acquire a knockdown and mortality rate near 100% is desirable to ensure effective protection of persons and property against general household pests.

Synergists are compounds that are non-toxic or negligibly toxic to a pest at a set dosage but are able to enhance the toxicity of the active chemical with which they are combined. Piperonyl butoxide (PBO) and N-Octyl bicycloheptene dicarboximide (MGK-264) are common insecticide synergists in commercial formulations. Although previously believed to be fairly non-toxic to mammals, indoor PBO use is being scrutinized by regulatory agencies and other groups for potential detrimental effects to humans and animals. MGK-264 is not as effective as PBO and is slightly more toxic.

The use of plant essential oils as insecticides has been reported, as described in U.S. Pat. Nos. 4,518,593, 7,534,447 and 6,231,865, and in U.S. Pub. No. 2013/0142893 (the full disclosures of which are incorporated herein by reference in their entireties). However, most natural products do not provide adequate control of pests particularly during large infestations. Consequently, there is a need in the art for novel synergistic and residual insecticidal compositions that addresses these concerns. The present invention provides these and relates advantages.

BRIEF SUMMARY

Embodiments of the present invention are directed to liquid insecticidal compositions for controlling a target pest and methods for use of the same. The present inventors have discovered that essential oils may act as synergists when used in combination with certain insecticides, for example when essential oils are employed as a solvent or co-solvent for solid insecticides. Accordingly, embodiments of the presently disclosed compositions have a higher insecticidal activity than the individual components and can be used at effective concentrations lower than expected based on the activity of the individual components. In various other embodiments, the composition resulting from combination of a solid insecticide and one or more essential oils (and/or constituents thereof) has properties ideally suited for use as an aerosolized insecticide.

In accordance with one embodiment, there is provided a liquid composition for controlling a target pest by aerosol application to a space in need thereof, the composition comprising a solid insecticide dissolved in a solvent comprising an essential oil, wherein the solid insecticide is selected from the group consisting of pyrethroid, neonicotinoid and halogenated pyrrole insecticides, and wherein the solid insecticide is present at a measurable concentration of at least 0.01% by weight of the composition.

Methods for use of the composition are also provided. For example, in another embodiment there is provided a method for controlling a target pest by aerosol application to a space in need thereof, the method comprising the step of aerosolizing an effective amount of the liquid composition disclosed herein, thereby contacting aerosol particles of the liquid composition with the space.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 1 is a bar graph comparing formulations of acetamiprid and rosemary oil (AR) and acetamiprid, rosemary oil and chlorfenapyr (ARC).

FIG. 2 is another bar graph showing knockdown efficacy for bed bugs on three chambers.

FIG. 3 presents residual efficacy data for a composition of acetamiprid and rosemary oil against bed bugs in three chambers.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Essential oil" is a concentrated hydrophobic liquid containing volatile aroma compounds from plants. Essential oils may contain a single component, or one or more major components together with one or more minor constituents. Essential oils within the context of the present disclosure include essential oils comprising mixtures of different constituents as well as essential oils which are enriched for one or more constituents or contain substantially a single essential oil constituent. Essential oils include essential oils, and constituents thereof, which are isolated from natural sources (e.g., plants) and/or prepared synthetically.

"Thyme oil" is an essential oil obtainable from the species of *Thymus*. Thyme oil includes oils and constituents thereof isolated from plant sources as well as prepared synthetically. The most common species of thyme, *Thymus vulgaris*, is a species of flowering plant in the mint family Lamiaceae, native to southern Europe. Thymol is usually the most abundant compound in thyme oil and can account for up to 50% of the total volume. Thyme oil composition may also contain high levels of other compounds, such as camphor, ρ-cymene, γ-terpinene, and caravacol, and lower levels of thymol. There are also a large number of compounds in trace amounts, including but not limited to, myrcene, α-pinene, camphene, borneol, β-caryophyllene, 1,3-octadiene, 1,7-acadiene, 2,4-dymethyl-2,4-heptadiene, sabinene, para-menthene-1, para-menthene-3, α-phellandrene, α-terpinene, limonene, (Z)-b-ocimene, (E)-b-ocimene, a-terpinolene, metha-3,8-diene, p-cimenen, trans-dihydrocarvone, thymol methyl ether, carvacrol acetate, b-caryophyllene, calamenene, gamma-cadinene, b-pinene, and linalool.

"Rosemary oil" is an essential oil obtainable from *Rommarinus officinalis, Limonium vulgare, Andromeda polifolia*, including substituents thereof. Rosemary oil includes oils and constituents thereof isolated from plant sources as well as prepared synthetically and includes, but is not limited to, pinene, borneol, camphor, bornyl acetate, camphene, terpineol, cineole, limonene, thujene, tricycele, diosmetin, diosmin, diterpenes, apigenin, genkwamin, hispidulin, isobutyl acetate, linalool, and/or lutiolin.

The term "methyl salicylate", also known as oil of wintergreen or wintergreen oil, is an organic ester naturally produced by many species of plant. Numerous plants produce methyl salicylate in small amounts; however, all species in the genera *Spiraea* and *Polygala*, and some in *Gaultheria* and *Beluta* produce larger quantities. Methyl salicylate can also be derived synthetically and is considered to be structurally and functionally equivalent to the naturally occurring wintergreen oil.

The term "insecticide" refers to a class of compounds which kills or causes knockdown of insects. A "solid insecticide" is an insecticide that exists is solid form at room temperature and pressure, and as opposed to a liquid or gaseous form. Representative insecticides include, but are not limited to, pyrethroid, neonicotinoid and halogenated pyrrole insecticides.

"Pyrethroid" insecticides are synthetic analogues of the naturally occurring pyrethrin I and pyrethrin II insecticides. Numerous pyrethroids are known in the art, including, but not limited to, allethrin, bifenthrin, bioallethrin, cyfluthrin, cypermethrin, cyphenothrin, deltamethrin, esfenvalerate, etofenprox, fenpropathrin, fenvalerate, flucythrinate, flumethrin, imiprothrin, λ-Cyhalothrin, metofluthrin, permethrin, prallethrin, resmethrin, silafluofen, sumithrin, τ-fluvalinate, tefluthrin, tetramethrin, tralomethrin and transfluthrin.

"Neonicotinoids" are a class of neuro-active insecticides chemically similar to nicotine. Representative neonicotinoids include, but are not limited to, acetamiprid, clothianidin, imidacloprid, nitenpyram, nithiazine, thiacloprid and thiamethoxam.

"Halogenated pyrrole" refers to a class of insecticides comprising a pyrrole ring having at least one halogen substituent on the pyrrole ring. A representative halogenated pyrrole is chlorofenapyr.

The term "acetamiprid" means N-[(6-chloro-3-pyridyl) methyl]-N'-cyano-N-methyl-acetamidine or (1E)-N-[(6-

Chlor-3-pyridinyl)methyl]-N'-cyan-N-methylethanimid-amid, CAS registry number 135410-20-7.

The term "imidacloprid" means 1H-Imidazol-2-amine, 1-[(6-chloro-3-pyridinyl)methyl]-4,5-dihydro-N-nitro-, CAS registry number 138261-41-3.

The term "chlorfenapyr" means 4-Bromo-2-(4-chlorophenyl)-1-ethoxymethyl-5-trifluoromethyl-1H-pyrrole-3-carbonitrile, CAS registry number 122453-73-0.

The term "target pest" refers to a pest, such as an insect, which is knocked down and/or killed by the disclosed compositions and methods.

The term "knockdown" or "knocking down" refers to the quick, short-term immobilization of the target pest.

The term "mortality" refers to the death of the target pest.

The term "moribundity" refers to the near death, such as incapable of coordinated movements, exhibiting only twitching of an appendages, of the target pest.

The term "lethality" or "lethal time" refers to the combination of both moribundity and mortality of the target pest.

The term "controlling" refers to damage to the pests, inhibition or modulation of pest growth, inhibition of pest reproduction by slowing or arresting its proliferation, or complete destruction/death of the pest.

The term, "solvent" refers a liquid substance capable of dissolving the solid insecticide into itself or one or more other substances.

A "synergist" is a compound which increases the insecticidal activity of a second compound. A synergist may itself have insecticidal activity or may be inactive.

The terms "control" or "controlling" are meant to include any insecticidal (killing) or insectistatic (inhibiting, maiming or generally interfering) activities of an insecticidal composition against a given pest. Thus, these terms not only include knocking down and killing, but also include such activities as those of chemisterilants which produce sterility in insects by preventing the production of ova or sperm, by causing death of sperm or ova, or by producing severe injury to the genetic material of sperm or ova, so that the larvae that are produced do not develop into mature progeny. The terms also include repellant activity that protect animals, plants or products from insect attack by making food or living conditions unattractive or offensive to pests. These repellant activities may be the result of repellents that are poisonous, mildly toxic, or non-poisonous to pests.

The term "insecticidally effective amount" is an amount of the compound of the invention, or a composition containing the compound, that has an adverse effect (e.g., knockdown and/or death) on at least 25% of the pests treated, more preferably at least 50%, most preferably at least 70% or greater. Preferably, an "effective pest-inhibiting amount" is an amount of the compound of the invention, or a composition containing the compound, where 25% or greater mortality against pests is achieved, preferably 50% or greater, more preferably 70% or greater mortality. Similarly, an "effective pest-growth modulating amount" is preferably one where 25% or greater pest-growth modulation is achieved, preferably 50% or greater, more preferably 70% of greater. The term "amount sufficient to prevent infestation" is also used herein and is intended to mean an amount that is sufficient to deter all but an insignificant sized pest population so that a disease or infected state is prevented.

The term "locus" or "space" refers to any location where control of insects is needed or expected to be needed.

I. Compositions

As noted above, the present disclosure provides compositions having activity as insecticides and which find utility in methods for knocking down and/or killing a target pest.

The present applicants have unexpectedly identified combinations of insecticides and essential oils having high insecticidal activity against target pests, such as bed bugs. In certain embodiments, the compositions are synergistic such that the insecticidal activity of the composition is greater than expected based on the insecticidal activity of the individual components.

Embodiments of the present invention are generally directed to compositions comprising an insecticide in combination with one or more essential oils, such as methyl salicylate, rosemary oil and/or thyme oil. The insecticide is typically a compound not found in essential oils or constituent thereof, and in some embodiments, is selected from the group consisting of pyrethroid, neonicotinoid and halogenated pyrrole insecticides. In some embodiments, the insecticide is a solid insecticide which is capable of dissolving in the essential oil and/or a solvent comprising the same.

Accordingly, in some embodiments the present invention provides a liquid composition for controlling a target pest by aerosol application to a space in need thereof, the composition comprising a solid insecticide dissolved in a solvent comprising an essential oil, wherein the solid insecticide is selected from the group consisting of pyrethroid, neonicotinoid and halogenated pyrrole insecticides, and wherein the solid insecticide is present at a measurable concentration of at least 0.01% by weight of the composition.

The concentration of the solid insecticide in the composition can vary and will generally be present in an insecticidal effective amount (i.e., an amount sufficient to cause knockdown and/or death of a target pest when the composition is applied to a space, for example by aerosol application). Typically, the solid insecticide concentrations range from 0.1% to 4% by weight of the composition. In some embodiments, the solid insecticide is present at a concentration of at least 0.1%, at least 1%, at least 2% or at least 3% by weight of the composition.

The solid insecticide can be chosen from various different classes of insecticides provided it has insecticidal activity against the target pest when combined with the other components of the composition. In certain embodiments of any of the compositions described herein, the solid insecticide is a pyrethroid insecticide. A pyrethroid is a synthetic analogue of naturally occurring insecticides found in pyrethrum. Many pyrethroids known in the art are suitable for use in the compositions. In certain embodiments, the pyrethroid insecticide is selected from the group consisting of allethrin, bifenthrin, bioallethrin, cyfluthrin, cypermethrin, cyphenothrin, deltamethrin, esfenvalerate, etofenprox, fenpropathrin, fenvalerate, flucythrinate, flumethrin, imiprothrin, λ-Cyhalothrin, metofluthrin, permethrin, prallethrin, resmethrin, silafluofen, sumithrin, τ-fluvalinate, tefluthrin, tetramethrin, tralomethrin and transfluthrin. For example, in some embodiments the pyrethroid insecticide is selected from the group consisting of resmerthrin, tetramethrin, bioallethrin and permethrin.

In certain other embodiments, the solid insecticide is a neonicotinoid insecticide. The neonicotinoid insecticide may be selected from neonicotinoid insecticides known in the art, for example in some embodiments the neonicotinoid insecticide is selected from the group consisting of acetamiprid, clothianidin, imidacloprid, nitenpyram, nithiazine, thiacloprid and thiamethoxam. In some exemplary embodiments, the neonicotinoid is imidacloprid. In other embodiments, the neonicotinoid is acetamiprid.

Halogenated pyrrole insecticides may also be present in certain embodiments of any of the disclosed compositions. In some of these embodiments, the halogenated pyrrole is chlorofenapyr.

In some embodiments, the compositions comprise two (or more) solid insecticides. For example, in some embodiments the composition comprises a neonicotinoid insecticide and a halogenated pyrrole insecticide. In some further embodiments, the composition comprises acetamiprid and chlorfenapyr.

The essential oil includes essential oils comprising a mixture of different constituents as well as purified or partially purified constituents of essential oils. Any essential oil, including constituents thereof, may be used in the present compositions. In some embodiments, an essential oil is selected which increases the solubility of the insecticide in the composition. In other embodiments, the essential oil is a synergist with respect to the solid insecticide such that the composition has an unexpectedly high insecticidal activity which is typically greater than the sum of its individual components. In various different embodiments, the essential oil itself has insecticidal activity. Exemplary essential oils and extracts, and constituents thereof, useful in the presently disclosed compositions include, but are not limited to: α-pinene, β-pinene, α-campholenic aldehyde, α-citronellol, α-iso-amyl-cinnamic (e.g., amyl cinnamic aldehyde), α-pinene oxide, α-cinnamic terpinene, α-terpineol (e.g., 1-methyl-4-isopropyl-1-cyclohexen-8-ol), λ-terpinene, achillea, aldehyde C16, α-phellandrene, amyl cinnamic aldehyde, allspice oil (pimento berry oil), amyl salicylate, anethole, anise oil, anisic aldehyde, basil oil, bay oil, benzyl acetate, benzyl alcohol, bergamot oil (extracted from plant species, such as, *Monardia fistulosa, Monarda didyma, Citrus bergamia, Monarda punctata*), bitter orange peel oil, black pepper oil, borneol, calamus oil, camphor oil, cananga oil, cardamom oil, carnation oil (e.g., *Dianthus caryophyllus*), carvacrol, carveol, cassia oil, castor oil, cedar oil (e.g., hinoki oil), cedar leaf oil, chamomile oil, cineole, cinnamaldehyde, cinnamic alcohol, cinnamon, cis-pinane, citral (e.g., 3,7-dimethyl-2,6-octadienal), citronella oil, citronellal, citronellol dextro (e.g., 3-7-dimethyl-6-octen-1-ol), citronellol, citronellyl acetate, citronellyl nitrile, *citrus unshiu* peel extract, clary sage oil, clove and clove bud oil (extracted from plant species, such as, *Eugenia caryophyllus* and *Syzgium aromaticum*), coriander oil, corn oil, cotton seed oil, d-dihydrocarvone, decyl aldehyde, diethyl phthalate, dihydroanethole, dihydrocarveol, dihydrolinalool, dihydromyrcene, dihydromyrcenol, dihydromyrcenyl acetate, dihydroterpineol, dimethyl salicylate, dimethyloctanal, dimethyloctanol, dimethyloctanyl acetate, diphenyl oxide, dipropylene glycol, d-limonene, d-pulegone, estragole, ethyl vanillin (e.g., 3-ethoxy-4-hydrobenzaldehyde), eucalyptol (e.g., cineole), *eucalyptus* oil (such as, *eucalyptus citriodora, eucalyptus globulus*), eugenol (e.g., 2-methoxy-4-allyl phenol), evening primrose oil, fenchol, fennel oil, fish oil, florazon (e.g., 4-ethyl α-α-dimethylbenzenepropanal), galaxolide, geraniol (e.g., 2-trans-3,7-dimethyl-2,6-octadien-8-ol), geraniol, geranium oil, geranyl acetate, geranyl nitrile, ginger oil, grapefruit oil (derived from the peel pink and white varieties of *Citrus paradise*) guaiacol, guaiacwood oil, gurjun balsam oil, heliotropin, herbanate (e.g., 3-(1-methyl-ethyl)bicyclo(2,2,1)hept-5-ene-2-carboxylic acid ethyl ester), hiba oil, hydroxycitronellal, 1-carvone, 1-methyl acetate, ionone, isobutyl quinoleine (e.g., 6-secondary butyl quinoline), isobornyl acetate, isobornyl methylether, isoeugenol, isolongifolene, jasmine oil, jojoba oil, juniper berry oil, lavender oil, lavandin oil, lemon grass oil, lemon oil, lime oil, limonene, linallol oxide, linallol, linalool, linalyl acetate, linseed oil, litsea cubeba oil, 1-methyl acetate, longifolene, mandarin oil, menthol crystals, menthol laevo (e.g., 5-methyl-2-isopropyl cyclohexanol), menthol, menthone laevo (e.g., 4-isopropyl-1-methyl cyclohexan-3-one), methyl anthranilate, methyl cedryl ketone, methyl chavicol, methyl hexyl ether, methyl ionone, mineral oil, mint oil, musk oil (such as, musk ambrette, musk ketone, musk xylol), mustard (also known as allylisothio-cyanate), myrcene, nerol, neryl acetate, nonyl aldehyde, nutmeg oil (extracted from the seed of the tree species *Myristica fragrans*), orange oil extract (extracted from fruit such as, *Citrus aurantium dulcis* and *Citrus sinensis*), orris oil (derived from *Iris florentina*) para-cymene, para-hydroxy phenyl butanone crystals (e.g., 4-(4-hydroxyphenyl)-2-butanone), palmarosa oil (derived from *Cymbopogon martini*), patchouli oil (derived from *Pogostemon cablin*), p-cymene, pennyroyal oil, pepper oil, peppermint oil (derived from *Mentha piperita*), perillaldehyde, petitgrain oil (extracted from the leaves and green twigs of *Citrus aurantium amara*), phenyl ethyl alcohol, phenyl ethyl propionate, phenyl ethyl-2-methylbutyrate, pinane hydroperoxide, pinanol, pine ester, pine oil, pinene, piperonal, piperonyl acetate, piperonyl alcohol, plinol, plinyl acetate, pseudo ionone, rhodinol, rhodinyl acetate, rose oil, rosemary oil (derived from *Rosmarinus officinalis*) sage oil (derived from *Salvia officinalis*), sandalwood oil (derived from *Santalum album*), sandenol, sassafras oil, sesame oil, soybean oil, spearmint oil, spice oils (such as, but not limited to, caraway seed oil, celery oil, dill seed oil, marjoram oil), spike lavender oil (derived from *Lavandula latifolia*), spirantol, starflower oil (also known as, borage oil), tangerine oil (derived from *Citrus reticulata*), tea seed oil, tea tree oil, terpenoid, terpineol, terpinolene, terpinyl acetate, tert-butylcyclohexyl acetate, tetrahydrolinalool, tetrahydrolinalyl acetate, tetrahydromyrcenol, thulasi oil, thyme oil, thymol, trans-2-hexenol, trans-anethole and metabolites thereof, turmeric oil, turpentine, vanillin (e.g., 4-hydroxy-3-methoxy benzaldehyde), vetiver oil, white cedar oil (derived from *Thuja occidentalis*), wintergreen oil (methyl salicylate) and the like.

In various embodiments, the essential oil is selected from the group consisting of methyl salicylate, rosemary oil, thyme oil, cinnamon oil, citronella oil, *eucalyptus* oil, lemongrass oil, orange oil. In other embodiments, the essential oil is selected from the group consisting of methyl salicylate, rosemary oil and thyme oil. In some embodiments, the essential oil is methyl salicylate. In some other embodiments, the essential oil is rosemary oil. In some embodiments, the essential oil is thyme oil. In some embodiments, the essential oil comprises methyl salicylate and thyme oil.

In some embodiments, the composition comprises thyme oil, and the thyme oil comprises a major constituent selected from the group consisting of thymol, camphor, ρ-cymene, γ-terpinene and caravacrol. In some other embodiments, the thyme oil comprises one or more minor constituent selected from the group consisting of myrcene, α-pinene, camphene, borneol, β-caryophyllene, 1,3-octadiene, 1,7-acadiene, 2,4-dymethyl-2,4-heptadiene, sabinene, para-menthene-1, para-menthene-3, α-phellandrene, α-terpinene, limonene, (Z)-b-ocimene, (E)-b-ocimene, α-terpinolene, metha-3,8-diene, p-cimenen, trans-dihydrocarvone, thymol methyl ether, carvacrol acetate, β-caryophyllene, calamenene, gamma-cadinene, β-pinene and linalool.

In still other embodiments of any of the disclosed compositions, the essential oil comprises a constituent selected from α-pinene, β-pinene, pulegone, anisole, eucalyptol, eugenol, geraniol, geranyl acetate, linalyl acetate, methyl anthranilate, myrcene, thymol and cymene.

In certain embodiments, the compositions further comprise additional ingredients selected to increase the insecticidal activity of the compositions. For example, synergists other than the essential oils are included in some embodiments. Accordingly, in some embodiments the compositions comprise a synergist selected from the group consisting of piperonyl butoxide, isopropyl myistate and phenethyl propionate.

The essential oil is present in the compositions in varying amounts, and will typically be present in an amount sufficient to aid in solubilizing the solid insecticide, enhance the insecticidal activity of the composition and/or optimize the physical properties of the compositions (e.g., ability to aerosolize). In some embodiments, the essential oil is present in an amount ranging from 0.01% to 99.99% by weight of the composition, and in another embodiment from about 1% to about 99% by weight of the composition. In other embodiments, the essential oil is the major component within the composition and present in an amount ranging from 95% to 99.9% by weight of the composition, for example from 96% to 99% by weight of the composition.

In some embodiments of any of the compositions described herein, the compositions comprise two essential oils. In such embodiments, the essential oil is typically present in the composition in an amount ranging from 1% to 99% by weight of the composition, for example an amount ranging from 40% to 60% by weight of the composition.

In certain other embodiments of the compositions, the compositions comprise thyme oil in an amount ranging from 40% to 90% by weight of the composition. In other embodiments, the compositions comprise methyl salicylate in an amount ranging from 10% to 60% by weight of the composition. In even more embodiments, the compositions comprise thyme oil in an amount ranging from 40% to 90% by weight of the composition and methyl salicylate in an amount ranging from 10% to 60% by weight of the composition. In still more embodiments, the compositions comprise thyme oil in an amount ranging from 30% to 70% by weight of the composition and methyl salicylate in an amount ranging from 5% to 50% by weight of the composition.

In some more specific embodiments of the compositions, the essential oil comprises rosemary oil, and the solid insecticide comprises acetamiprid or chlorfenapyr or both. In some of the embodiments, the compositions comprise rosemary oil, acetamiprid and chlorfenapyr.

In still other embodiments, the essential oil comprises methyl salicylate and thyme oil, and the solid insecticide is imidacloprid. For example, certain embodiments are directed to compositions comprising from 0.1% to 4% imidacloprid, 5% to 50% methyl salicylate and 30% to 70% thyme oil, wherein the percentages are by weight of the composition.

In an embodiment, the composition of the present invention comprises rosemary oil and/or its constituents in an amount ranging from 5.0% by weight to 50.0% by weight and acetamiprid in an amount ranging from 0.10% by weight to 2.0% by weight and/or chlorfenapyr in an amount ranging from 0.10% by weight to 1.0% by weight. For controlling bed bugs, a preferred liquid insecticide composition of the present invention comprises 1.0-2.0% acetamiprid by weight, 0.10-1.0% by weight of chlorfenapyr and 10.0-50.0% by weight of rosemary oil. Such formulations may also include carriers such as tween and propylene glycol.

The compositions are effective to knockdown and/or kill a wide range of target pests. One of ordinary skill in the art can select the correct combination of solid insecticide and essential oil components based on the desired target pest.

The insecticidal compositions and methods of the present invention are effective in the control of different species of invertebrate pests. It will be understood that the pests exemplified and evaluated in the examples herein is representative of such a wider variety. By way of illustration, but not limitation, the insecticidal compositions of the present invention are also useful for control of pests such as fleas (Siphonaptera), mosquitos (Diptera: Culicidae), yellow jackets and wasps (Hymenoptera: Vespidae), bees, (Hymenoptera: Apoidea), ants (Hymenoptera: Formicidae), cockroaches (Blattodea: Blaberoidea), termites (Blattodea: Isoptera), insect agricultural/plant pests such as leafhoppers (Heteroptera: Cicadellidae), stink bugs (Heteroptera: Pentatomidae), beetles (Coleoptera), moths (Lepidoptera), lygus bugs (Heteroptera: Miridae: Lygus), leaf miner flies (Diptera: Agromyzidae), whiteflies (Homoptera: Aleyrodidae), *thrips* (Thysanoptera), and aphids (Homoptera: Aphididae), in addition to arachnids, such as spiders (Araneae), ticks and mites (Acari), slugs and snails (Molluska: Gastropoda), nematodes, water-molds (Heterokontophyta: Oomycota, e.g. species in the *Phytophthora* and *Pythium* genera), bacteria (e.g. *Erwinia* genus), as well as fungi, in the Ascomycota, Chytridiomycota, and Zygomycota phyla (e.g. Clavicipitaceae, Davidiellaceae, Diatrypaceae, Mycosphaerellaceae, Mucoraceae, and Sclerotiniaceae Families), but not excluding other phyla, classes, orders, or families, such as true smut fungi (Ustilaginomycetes), pathogenic fungi (Pucciniales), molds (Dermatophytes), and the Ceratobasidiaceae family in the Basidiomycota phylum.

Further targeted pests controlled by the insecticidal composition of the present invention are, for example, members of Diplopoda (millipedes), e.g. the spotted snake millipede (*Blaniulus guttulatus*); Chilopoda (centipedes), e.g. soil centipedes (Geophilomorpha: Geophilidae), house centipedes (Scutigeromorpha), and tropical centipedes (Scolopendromorpha); Symphyla (symphylans/pseudocentipedes), e.g. the garden centipede (Scutigerella immaculate); Collembola (springtails and allies); and Isopoda (isopods), e.g. woodlice (Oniscidea), and pillbugs (Oniscidea: Armadillidiidae). Within the Class Insecta, examples of target pests include those in the Orders, Zygentoma (silverfish), e.g. Oriental silverfish (*Ctenolepisma villosa*), firebrat (*Thermobia domestica*), and common silverfish (*Lepisma saccharina*); Microcoryphia (bristletails); Dermaptera (earwigs), e.g. shore earwig (*Labidura riparia*) and European earwig (*Forficula auricularia*); Orthoptera (grasshoppers, crickets, katydids), e.g. house cricket (*Acheta domesticus*), camel cricket (Rhaphidophoridae), Oriental migratory locust (*Locusta migratoria*), and mole cricket (Gryllotalpidae); Blattodea (cockroaches and termites), e.g. American cockroach (*Periplaneta americana*), German cockroach (*Blattella germanica*), Oriental cockroach (*Blatta orientalis*), rottenwood termites (Archotermopsidae), drywood termites (Kalotermitidae), harvester termites (Hodotermitidae), subterranean termites (Rhinotermitidae), and higher termites (Termitidae); Thysanoptera (*thrips*), e.g. western flower thrip (*Frankliniella occidentalis*), onion thrip (*Thrips tabaci*), and melon thrip (*Thrips palmi*); Psocodea (barklice, booklice, and parasitic lice), e.g. larger pale booklouse (*Trogium pulsatorium*), chewing lice (Mallophaga), and sucking lice (Anoplura) such as the crab louse (*Phthiris pubis*), human louse (*Pediculus humanus*) and pale lice (Linognathidae). Also included are members of Hemiptera, e.g. stink bugs (Pentatomidae), rice bug (*Cletus punctiger*), common bed bug (*Cimex lectuarius*), tropical bed bug (*Cimex hemipterus*), cotton stainer (*Dysdercus intermedius*), kissing bugs (Triatominae), whiteflies (Aleyrodidae) such as the silverleaf whitefly (*Bemisia tabaci*), aphids (Aphididae) such as black bean aphid (*Aphis fabae*), cabbage aphid (*Brevicoryne brassicae*) and green peach aphid (*Myzus persicae*), leafhoppers (Cicadellidae) such as the potato leafhopper (*Empoasca fabae*), grape leafhopper (*Erythroneura comes*) and brown rice planthopper (*Nilaparvata lugens*), soft scale insects (Coccidae) such as the brown scale (*Lecanium corni*) and black scale (*Saissetia oleae*), armored scale insects (Diaspididae) such as the California red scale (*Aonidiella aurantii*), and mealybugs (Pseudococcidae); Coleoptera (beetles), including but not limited to scarab beetles (Scarabaeidae), metallic wood-boring beetles (Buprestidae), click beetles (Elateridae), carpet beetles (Dermestidae), horned powder-post beetles (Bostrichidae), death-watch beetles (Ptinidae), sap-feeding beetles (Nitidulidae), darkling beetles (Tenebrionidae), long-horned beetles (Cerambycidae), leaf beetles (Chrysomelidae) such as the bean weevil (*Acanthoscelides obtectus*) and Colorado potato beetle (*Leptinotarsa decemlineata*), and snout and bark beetles (Curculionidae) such as the black vine weevil (*Otiorhynchus sulcatus*) and Alfalfa weevil (*Hypera postica*); Hymenoptera (ants, bees, and wasps), e.g. conifer sawflies (Diprionidae), common sawflies (Tenthredinidae), paper wasps (Vespidae: Polistinae), and ants (Formicidae) such as odorous ants (Dolichoderinae), fire ants (*Solenopsis*), the pharaoh ant (*Monomorium pharaonis*), Argentine ant (*Linepithema humile*) and carpenter ants (*Camponotus*); Lepidoptera (butterflies and moths), e.g. tussock moths (Lymantriidae) such as the gypsy moth (*Lymantria dispar*), torticid moths (Torticidae) such as the oak leafroller moth (*Tortrix viridana*), crambid snout moths (Crambidae) such as the Mediterranean flour moth (*Ephestia kuehniella*), leaf blotch miner moths (Gracillariidae) such as the citrus leafminer (*Phyllocnistis citrella*), owlet moths (Noctuidae) such as the cabbage armyworm (*Mamestra brassicae*), clothes moths (Tineidae), and tent caterpillars and lappet moths (Lasiocampidae); and Diptera (flies), e.g. mosquitoes (Culicidae), black flies (Simuliidae), biting midges (Ceratopogonidae), vinegar flies (Drosophilidae), house flies (Muscidae), root-maggot flies (Anthomyiidae) such as the beet leafminer (*Pegomya hyoscyami*), bee lice (Braulidae), louse flies (Hippoboscidae), tsetse flies (Glossinidae), blow flies (Calliphoridae) such as cluster flies (*Pollenia*) and hairy maggot blow flies (*Chrysomya*), bot flies (Oestridae), fruit flies (Tephritidae) such as the Mediterranean fruit fly (*Ceratitis capitata*), large crane flies (Tipulidae) such as the European crane fly (*Tipula paludosa*), horse flies (Tabanidea), and sand flies (Psychodidea).

Other exemplary target pests include, but are not limited to, cockroaches (Blattodea: Blaberoidea), American cockroach (*Periplaneta americana*), German cockroach (*Blattella germanica*), Oriental cockroach (*Blatta orientalis*)), flies (Diptera) (e.g., housefly (*Musca domestica*), blow flies (*Calliphoridae* spp.), flesh flies (*Sarcophagidae* spp.), stable fly (*Stomoxys calcitrans*), fruit flies (*Drosophila* spp.) humpback flies (*Phoridae* spp.), drain flies (*Psychodidae* spp.), fungus gnats (*Sciaridae* spp. and *Fungivoridae* spp.), cluster fly (*Pollenia rudis*), black flies (*Silmulium* spp.), biting midges (Ceratopogonidae), deer flies (*Chrysops* spp. and *Silvius* spp.), snipe flies (*Symphoromyia* spp.), ants (Hymenoptera: Formicidae) (e.g., odorous house ant (*Tapinoma sessile*) carpenter ant (*Camponotus* spp.)), silverfish (Zygentoma), camel crickets (Rhaphidophoridae), spiders (Araneae), ticks and mites (Acari), bed bugs (*Cimex lectuarius* and *Cimex hemipterus*), fleas (Siphonaptera), earwigs (Dermaptera), termites (Blattodea: Isoptera), lice (Phthiraptera), spiders (Arachidae), mites and ticks (Acari) wasps and bees (Hymenoptera: Vespidae and Apoidea). In some embodiments, the target pest is selected from the group consisting of bed bugs (*Cimex* spp), fleas (Siphonoptera), lice (Phthiraptera), silverfish (Zygentoma), crickets (Orthoptera), cockroaches (Blattodea: Blaberoidea), ants, wasps, and bees (Hymenoptera: Fomiciadae, Vespidae, and Apoidea), and flies (Diptera). For example, in some embodiments the target pest is a bed bug (*Cimex lectularius*), such as a pyrethroid-resistant bed bug.

The compounds described (e.g., insecticides, essential oils and constituents thereof) herein are meant to include all racemic mixtures and all individual enantiomers or combinations thereof, whether or not they are specifically depicted or described herein. Further, the compounds are also intended to include all tautomeric forms and salts, even if not specifically depicted or described. Tautomers are compounds which result from the formal migration of a hydrogen atom or proton, accompanied by a switch of a single bond and adjacent double bond.

The insecticidal compositions of the present invention are advantageous in that they can typically control pests at average or lower than average dosage rates. Such insecticidal compositions are also advantageous in that they can provide extended protection to a locus. Further, embodiments of such insecticidal compositions are also advantageous in that said insecticidal compositions control pests without introducing a notable amount of harm to the surrounding environment of which the provided insecticidal composition is being utilized.

The insecticidal compositions of the invention have insecticidal activity against one or more pests. However, it is understood that certain insecticidal compositions may be more effective on some pests than others, and may even be ineffective against some pests. However, that does not in any way detract from their value as insecticides since the present invention contemplates use as broad, general acting insecticides, while others have utility as specific or selective insecticides. The non-limiting examples set forth below illustrate methods by which the broad-acting or selectivity of insecticidal activity may be readily ascertained by routine experimentation.

The insecticidal compositions of the present invention offer several advantages over currently used insecticides. For example, the essential oils used in the composition of the invention are generally naturally occurring compounds (or synthetically prepared versions of the same), and as such are regarded as minimally toxic to humans, domestic animals and wildlife. Accordingly, by using the subject compositions, the environmental and health hazards involved in pest control are minimized. Because of the versatility and broad spectrum of the present compositions, when necessary, the composition can be used as a preventative on a repeated basis and, thus, can be integrated into integrated pest management (IPM) programs.

In one aspect, the compositions comprise surfactants which may aid in delivery of the compositions, for example by aerosol delivery. The presence of nonionic, cationic or anionic surfactants, such as, sodium lauryl sulfate, nonyl phenoxypolyoxyethylene and hydrogenated tallow dimethyl benzyl ammonium chloride, can be used as adjuvants. In certain embodiments, the adjuvants are believed to confer increased insecticidal activity on the composition by acting as a wetting, dispersing and/or emulsifying agent that facilitates or aids in the spreading of the insecticide and/or essential oil across an insect or larva, providing for a more uniform and rapid penetration of through the exoskeleton (if present), thus permitting the insecticide and/or essential oil to exert their insecticidal activity on the internal organs and/or nervous system of the insect or larva. Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers. Non-limiting examples of anionic surfactants include salts of fatty acids, alkyl sulphates, alkyl ether sulphonates and alkyl aryl sulfonates. Other examples of preferred surfactants include sodium dodecyl benzenesulfonic acid, alcohol ethoxylate, olefin sulfonate, and modified phthalic glycerol alkyd resins.

Use of insecticidal compositions of the present invention generally results in fast knockdown and high (e.g., up to 100%) mortality on contact. As such, they are advantageously employed as insecticidal agents in uses such as, without limitation, households, hotels, lawn and garden applications, agriculture, organic farming, greenhouse/nursery applications, stored product applications, professional pest control, pet bedding, foliage application, underwater or submerged application, solid treatment, soil incorporation application, seedling box treatment, stalk injection and planting treatment. In certain embodiments, the compositions are employed for control of pests in interior living spaces, such as residential and/or or hotel living spaces.

The compositions optionally comprise one or more carriers. The term "carrier" as used herein refers to a solid or fluid material, which may be inorganic or organic and of synthetic or natural origin, with which the compositions are mixed or formulated to facilitate their application to the desired space, or its storage, stability, transport and/or handling. The insecticidal compositions of the instant invention typically comprise an inert carrier, in an amount in which the inert carrier can assist the composition to be carried through a process or method of controlling pests. As such an amount of the inert carrier, the inventive insecticidal compositions preferably comprise the inert carrier in an amount of from about 0.1%-99.9% by weight of the composition. Non-limiting examples of carriers that may be in the insecticidal compositions of the instant invention include water, alcohols such as methanol and ethanol, aromatic hydrocarbons such as toluene, xylene, ethylbenzene and alkyl naphthalenes, non-aromatic hydrocarbons such as hexane, cyclohexane, kerosene, isoparaffinic and normal paraffinic solvents and light oils, esters such as ethyl acetate and butyl acetate, nitriles such as acetonitrile and isobutylonitrile, ethers such as diisopropyl ether and dioxane, amides such as N,N-dimethylformamide and N,N-dimethylacetamide, halogenated hydrocarbons such as dichloromethane, trichloroethane and carbon tetrachloride, dimethylsulfoxide, botanical oils such as soy oil and cotton seed oil, and the like, and a mixture thereof. Examples of the gas carriers that may be in the aerosol form of insecticidal compositions of the instant invention include propellants such as air, nitrogen, butane gas, propane gas, liquid petroleum gas, dimethyl ether, carbon dioxide, and the like, and a mixture thereof.

In general, any of the materials customarily employed in formulating insecticides are suitable for use in the present compositions. The inventive insecticidal compositions of the present invention may be employed alone or in the form of mixtures with solid and/or liquid dispersible carrier vehicles and/or other known compatible active agents such as other insecticides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The insecticidal compositions of the present invention can be formulated or mixed with, if desired, conventional inert insecticide diluents or extenders of the type usable in conventional insecticide formulations or compositions, e.g. conventional insecticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc. In addition, mineral oil and the essential oils disclosed herein (e.g., thyme oil, rosemary oil, methyl salicylate, safflower oil, benzyl alcohol, citronellal, d-limonene, soybean oil, sesame oil, etc.) may also serve as diluents or carriers in the insecticidal compositions of the present invention.

Further, the insecticidal compositions of the instant invention may additionally contain a coloring agent, a formulation auxiliary, or a combination thereof. As such, examples of such coloring agents that may be utilized in the insecticidal compositions of the instant invention include inorganic pigments such as metal oxides, titanium oxides and Prussian blue, organic dyes such as alizarine dyes, azo dyes and metallic phthalocyanine dyes, iron, manganese, boron, copper, cobalt, molybdenum, zinc and salts thereof, and the like, or a mixture thereof and examples of such formulation auxiliaries that may be utilized in the insecticidal compositions of the instant invention include attaching and/or dispersing agents, surfactants, stabilizers, and the like, or a mixture thereof.

Use of insecticides is regulated in the United States by the Environmental Protection Agency (EPA) under authority of the Federal Insecticide, Fungicide and Rodenticide Act (FIFRA). Tolerance for residues of insecticides in agricultural commodities are established by the (EPA) and enforced by the Food and Drug Administration (FDA) under authority of the Federal Food, Drug and Cosmetic Act (FD&C Act). This regulatory environment leads to another aspect of this invention, which is an article of manufacture. In this aspect a composition of the present invention may be sold in a container that will be suitable for storing the composition for its shelf life. Associated with the container is printed instructions and/or a printed label indicating that the subject composition can be used to control pests, i.e., used as an insecticide and providing instructions for using the composition for insecticidal purposes in accordance with the treatment methods set forth herein. The container may have associated with it a delivery device (e.g., aerosol device) that allows the composition to be applied to the pest population or to the area to be treated. The container may be made of any suitable material such as a polymer, glass, metal, or the like. Usually, the labeling is associated with the container by being adhered to the container, or accompanying the container in a package sold to the user. Such label may indicate that the composition is approved for use as an insecticide. The instructions will spell out the type of pests for which the insecticidal composition is to be used, the application method, the rate of application, dilution requirements, use precautions, and the like.

The efficacy of the insecticidal compositions of the present invention may be monitored by determining the mortality of or damage (e.g., knockdown) to the pest population, i.e., by determining its adverse effect upon treated pests. This includes controlling to the pests, by inhibition or modulation of pest growth, inhibition of pest reproduction by slowing or arresting its proliferation, or complete destruction/death of the pest, all of which are encompassed by the term "controlling". The actual value of an insecticidally effective amount for a given compound is preferably determined by routine screening procedures employed to evaluate insecticidal activity and efficacy, such as are well known by those skilled in the art and as are described in the Examples. It is expected that compositions of the invention having a higher level of insecticidal activity can be used in smaller amounts and concentrations, while those having a lower level of activity may require larger amounts or concentrations in order to achieve the same insecticidal effect. Efficacy is also monitored by any adverse effects that might be experienced by a human user who is applying the composition to an infested area. Accordingly, the amount of composition used in the methods of the invention, meets the mortality, modulation or prevention criteria above, and preferably has minimal or no adverse effect on ornamental and agricultural plants (such as phytotoxicity), wildlife and humans that may come into contact with the composition.

The solid insecticides (e.g., pyrethroid, neonicotinoid and halogenated pyrrole insecticides) for use in the present compositions and methods may be purchased from commercial sources or prepared synthetically using techniques known in the art.

The essential oils and constituents thereof are known and used for other uses, they may be prepared by a skilled artisan by employing known methods and/or isolated from natural sources using common techniques.

Formulations containing the insecticidal compositions of the present invention may be prepared in any known manner, for example by admixture of the solid insecticide and one or more essential oils or constituents thereof and optionally carriers and/or surfactants.

The compositions of the present invention may be derived from commercially available formulations of insecticides. Chlorfenapyr, sold by BASF Corporation under the names and trademark of Phantom® Termiticide/Insecticide or Pylon® TR Total Release Insecticide, and acetamiprid sold under the name and trademark of TriStar®. Imidacloprid is sold by Bayer Corporation, Control Solutions Inc, Ensystex, MGK and others under various names and trademarks, such as but not limited to, Prothor®, Bithor®, Temprid®, Dominion®, Bedlam®. The above-mentioned formulations of insecticides can be dispersed in an aqueous medium with an essential oil, which is typically commercially available, to provide a composition containing an effective insecticide formulation that is within the scope of the present invention.

II. Methods

Embodiments of the present invention are directed to use of any of the compositions described herein for controlling a target pest. The methods for controlling a target pest generally comprising contacting a space in need thereof with a composition as described herein. The instant compositions may be applied in any suitable usual manner, for instance by spraying, atomizing, vaporizing, scattering, dusting, watering, squirting, sprinkling, pouring, fumigating, and the like, provided the method is sufficient to contact the space with an insecticidally effective amount of the composition. In some embodiments, the composition is dispersed as an aerosol. For example, in some embodiments a method for controlling a target pest by aerosol application to a space in need thereof is provided, the method comprising the step of aerosolizing any of the liquid compositions disclosed herein, thereby contacting an insecticidally effective amount of the liquid composition with the space.

In certain embodiments of the foregoing method, at least 90% of the total aerosol particles are less than 1.3±0.5 µm in diameter when aerosolized. In other embodiments, the particle size of the aerosol particles is such that at least 90% of the aerosol particles have a diameter of 0.7±0.2 µm or less within 60 seconds of being aerosolized.

In other embodiments of the method, the liquid composition is aerosolized in an amount ranging from an aerosol number concentration value ranging from 100 counts/cm$^3$ to 45,000 counts/cm$^3$ or an aerosol mass concentration value ranging from 0.01 mg/m$^3$ to 10 mg/m$^3$.

The time which the composition is aerosolized will depend on several factors, including the size of the space and the target pest. One of ordinary skill in the art can determine a suitable time for aerosolization. In some embodiments, the liquid composition is aerosolized for a time ranging from 5 minutes to 24 hours, for example from 1 hour to 6 hours.

The method can be used to control a variety of target pest species, including any of the target pests described herein above. In some embodiments, the target pest is selected from the group consisting of bed bugs (*Cimex* spp), fleas (Siphonoptera), lice (Phthiraptera), silverfish (Zygentoma), crickets (Orthoptera), cockroaches (Blattodea: Blaberoidea), ants, wasps, and bees (Hymenoptera: Fomiciadae, Vespidae, and Apoidea), and flies (Diptera). For example, in some embodiments the target pest is a bed bug (*Cimex lectularius*), such as a pyrethroid-resistant bed bug.

The method finds utility in any space in need of controlling a target pest, including interior and exterior spaces. In some embodiments, the space is an interior space, such as a residence, hotel rooms, public transportation, retail stores, entertainment venues, shelters, detention facilities, health care facilities, fitness facilities, animal care facilities, agricultural facilities, food processing facilities, storage facilities, educational/training facilities, industrial space, commercial space, or office space. In some embodiments, the interior space is a location that provides refuge for target pests. In some embodiments, the interior space comprises a location that is characterized as warm, low lighting, and includes furniture, such as a bed.

The methods of use of the insecticidal compositions of the invention will depend at least in part upon the pest to be treated and its feeding habits, as well as breeding and nesting habits. While a minor dose of the novel compositions will have an adverse effect on pests, adequate control involves the application of a sufficient amount to either eliminate pests entirely or significantly deter their growth and/or rate of proliferation. Dosage required to accomplish these effects, of course, vary depending on the target pest, size, and maturity, i.e., stage of growth. Certain pests or their eggs may be more resistant to insecticides and require higher dosage for a comparable level of control. Dose response experiments using different dilutions (for example, about 1:1000, 1:100, 1:10 and 1:3) of the insecticidal compositions of the present invention on target organisms are performed to determine the optimal concentration of the solid insecticide and solvent.

The following Examples are provided for purpose of illustration and not limitation.

EXAMPLES

The following examples set forth certain biological data illustrating the efficacy of the compositions of the present invention in controlling general household pests. Each experiment embodies a separate test wherein the pests were randomly selected from both colony reared and wild populations. When aerosolized, two spray chambers were used in the experiments. Chamber one was a non-porous glass chamber approximately 1300 cubic in., which is divided into three separate compartments. Each compartment is restricted by a small 4 cm hole from the previous compartment, and therefore receives less of the formulation. The volume of the separate compartments were as follows: compartment 1: 430 cubic in.; compartment 2: 460 cubic in., compartment 3: 430 cubic in. Chamber two was a polypropylene container with a 114 L capacity. An aerosol control apparatus (either an AirQ 550 or custom AirQ system) manufactured by Prolitec located in Milwaukee, Wis. were used in the testing of bed bugs.

Example 1

Bed Bug Lethal Time at 50% and 99% of Variations of Combinations of Acetamiprid, and/or Chlorfenapyr, and Rosemary Oil on Contact and Residual Efficacy The compositions of the present invention were tested for bed bug insecticidal activity in the following manner.

The compositions and individual components thereof were prepared to provide the appropriate rates of application for combinations of acetamiprid, chlorfenapyr, and rosemary oil, as well as acetamiprid, chlorfenapyr, and rosemary oil paired and alone. The insecticide formula(s) were aliquoted (100 μL) into a glass petri dish (100 mm). Filter paper was placed on top of the solution. Ten adult bed bugs were then placed on top of the filter paper and morbidity and moribundity (knockdown) and mortality was recorded at 5 minutes for each treatment combination and the control. After 2 hours, bed bugs were removed from the treated surface and placed in a holding chamber. Bed bug morbidity, moribund, and mortality was recorded every 24 hours for 7 days. Data from this experiment is presented in Table I.

TABLE I

Time required for 50% (LT50) and 99% (LT99) lethal and residual effects of compositions comprising Acetamiprid, and/or Chlorfenapyr, and Rosemary Oil on a nonresistant strain of bed bug.

| Treatment | Rate (% by weight) | 2 hour exposure (min) | | Residual Effect (% Knockdown & Mortality/hrs) | | |
|---|---|---|---|---|---|---|
| | | LT50 | LT99 | 24 | 48 | 72 |
| Acetamiprid | 1.0 | 7.0 | 510.8 | 40.0 | 30.0 | 50.0 |
| | 0.1 | 22.4 | 12565.9 | 20.0 | 10.0 | 10.0 |
| | 0.01 | 39.3 | 38038.1 | 10.0 | 20.0 | 20.0 |
| Chlorfenapyr | 1.0 | — | — | 40.0 | 80.0 | 100.0 |
| | 0.1 | — | — | 30.0 | 50.0 | 70.0 |
| | 0.01 | — | — | 0.0 | 0.0 | 0.0 |
| Rosemary Oil | 35.0 | 22.3 | 173.1 | 90.0 | 90.0 | 90.0 |
| | 25.0 | 23.6 | 247.5 | 60.0 | 40.0 | 40.0 |
| | 0.1 | 11.1 | 713.8 | 40.0 | 40.0 | 40.0 |
| Acetamiprid/ Rosemary Oil | 0.5/25.0 | 5.3 | 195.2 | 60.0 | 40.0 | 30.0 |
| | 1.0/10.0 | 4.0 | 9.2 | 70.0 | 70.0 | 70.0 |
| Chlorfenapyr/ Acetamiprid | 1.0/0.1 | 228.0 | >50000.0 | 0 | 20.0 | 40.0 |
| Chlorfenapyr/ Rosemary Oil | 1.0/10.0 | 98.5 | 6575.7 | 40.0 | 40.0 | 100.0 |
| Acetamiprid/ Chlorfenapyr Rosemary Oil | 1.0/0.1/10.0 | 8.3 | 108.7 | 90.0 | 100.0 | 100.0 |
| Control (Acetone) | 100.0 | — | — | 0.0 | 0.0 | 0.0 |

Dash indicates no knockdown or mortality during exposure.

The data in Table I demonstrate the definite synergitic and increased residual toxicity of rosemary oil with known active insecticidal compounds. This increase in efficacy is unexpected and significant.

Example 2

Figure 1:
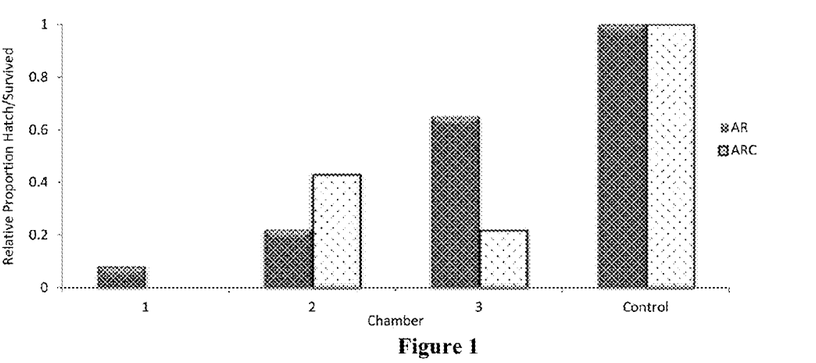

Determining the Efficacy of Combinations of Acetamiprid, and/or Chlorfenapyr, and Rosemary Oil Against Bed Bug Eggs Compositions were prepared to provide the appropriate rates of application of the a formulation of acetamiprid and rosemary oil, as well as a combined formulation of acetamiprid, chlorfenapyr and rosemary oil. Compositions were aliquoted (100 ml) into a Prolitec aerosol generating device. Four replicates of approximately 20 to 40 bed bug eggs in a small colony jar were placed in each one of the 3 chambers and one placed outside the chamber to be used for the control. The Prolitec controlled aerosol apparatus was set for continuous output for a period of 60 minutes. The four treated colony jars containing immature bed bugs and bed bug eggs were given the opportunity to blood feed, by offering them defibrinated rabbit blood in an artificial feeder. One week after feeding, the number of dead, the number of unhatched eggs, and the number of living bed bugs was counted. Data is presented in Tables II and III. Comparative data for the Acetamiprid/Rosemary composition and Acetamiprid/Chlorfenapyr/Rosemary composition is presented in FIG. 1.

TABLE II

Combination formulation of Acetamiprid and Rosemary Oil. Number of eggs per treatment, shown with the proportion hatched and the proportion that survived.

| Chamber | No. of Eggs | No. Hatched | Proportion Hatched | No. Alive | Proportion Survived |
|---|---|---|---|---|---|
| 1 | 38 | 25 | 0.66 | 2 | 0.053 |
| 2 | 30 | 18 | 0.6 | 24 | 0.133 |
| 3 | 24 | 23 | 0.96 | 15 | 0.625 |
| Control | 40 | 40 | 1.0 | 40 | 1.0 |

Bed bugs that survived were able to molt and feed.

TABLE III

Combination formulation of Acetamiprid, Chlorfenapyr and Rosemary Oil. Number of eggs per treatment, shown with the proportion hatched and the proportion that survived.

| Chamber | No. of Eggs | No. Hatched | Proportion Hatched | No. Alive | Proportion Survived |
|---|---|---|---|---|---|
| 1 | 39 | 32 | 0.82 | 0 | 0.0 |
| 2 | 23 | 21 | 0.91 | 9 | 0.391 |
| 3 | 36 | 23 | 0.64 | 5 | 0.139 |
| Control | 40 | 40 | 1.0 | 40 | 1.0 |

Bed bugs that survived were able to molt and feed.

These data demonstrate the definite synergistic and increased residual toxicity of rosemary oil with known active insecticidal compound against bed bug eggs. This increase in efficacy is significant and unexpected.

Example 3

Determination of Active and Residual Efficacy of Bed Bug Knockdown and Mortality Rates of Combinations of Acetamiprid, and/or Chlorfenapyr, and Rosemary Oil by Aerosol Compositions were prepared to provide the appropriate rates of application of combinations of acetamiprid and rosemary oil (AR), as well, acetamiprid, chlorfenapyr, and rosemary oil paired (ARC). Composition were formulated together with typical carriers such as tween and propylene glycol. The compositions were aliquoted (100 ml) into a Prolitec aerosol generating device. Ten adult bed bugs in 60 mm glass petri dishes were placed in each of the 3 compartments in the glass chamber and one placed outside the chamber to be used for the control. The Prolitec controlled aerosol apparatus. The Prolitec controlled aerosol apparatus was set for continuous output for a period of 2 hours. Bed bugs were observed for morbidity, moribundity, and mortality every 5 minutes for 2 hours. After 2 hours, the bed bugs were removed from the test chamber and observed every 24 hours for 7 days to determine morbidity, moribundity, and mortality. The experiment was repeated three times. The mean aerosol output rate for the three AR experiments (0.031±0.008) and the three ARC experiment (0.026±0.008) was not significantly different ($p<0.05$).

Figure 2:
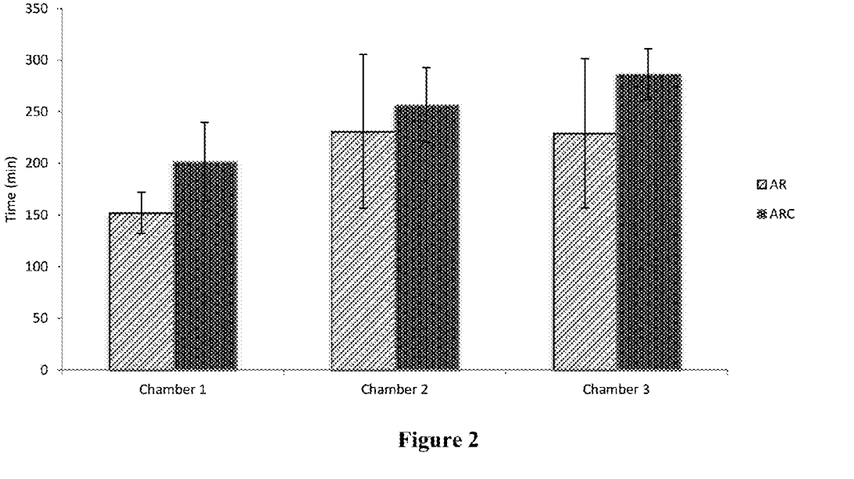

FIG. 2 is a bar graph showing data of insecticidal knockdown efficacy in chambers 1, 2, and 3 for each formulation in three separate trials. Lethal time (LT50) was based on visual observations only, no prodding was used to determine finite status. Mean and standard deviation are shown.

Figure 3:
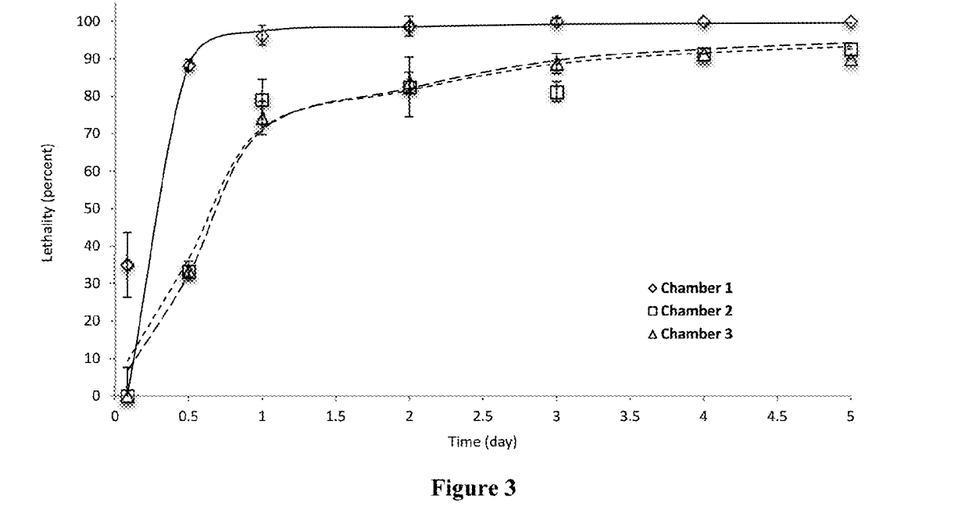
Figure 4:
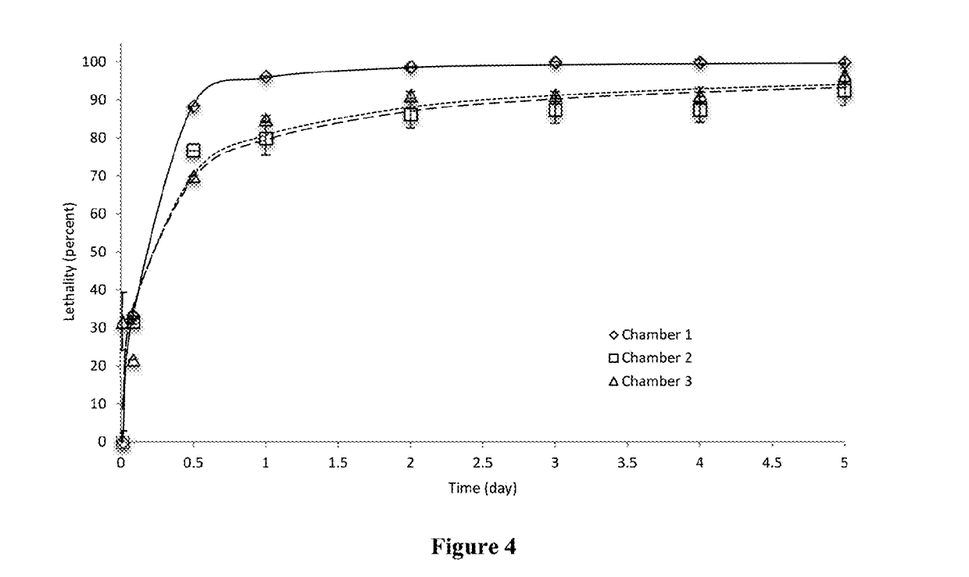
FIG. 4 provides residual efficacy data for a composition of acetamiprid, rosemary oil and chlorfenapyr against bed bugs in three chambers.

FIG. 3 shows residual efficacy of the insecticide composition, acetamiprid and rosemary against bed bugs in chambers 1, 2, and 3. The mean with standard deviation of 3 separate trials is shown. FIG. 4 presents similar data for the acetamiprid/chlorfenapyr/rosemary composition.

The foregoing data provides evidence that Rosemary oil synergizes both with acetamiprid and chlorfenapyr, alone or when combined in formulation. These effects were significant and provide an advantage over existing pesticide and technologies by reducing the amount of pesticide product needed as well as overall efficacy.

Example 4

Synergistic Effects of Rosemary Oil on Pyrethroids

Compositions comprising rosemary oil and/or pyrethroids were aliquoted (100 μL) into a glass petri dish (100 mm). The control is 100 μL acetate. Filter paper was then placed on top of the solution. Ten adult bed bugs resistant strain (UMC) colony were than placed on top of the filter paper and morbidity and moribundity (knockdown) and mortality was recorded at 5 minutes for each treatment combination and the control. After 2 hours, the bed bugs were removed from the treated surface and placed in a holding chamber. Bed bugs morbidity, moribund, and mortality was recorded every 24 hours for 7 days. Results are provided in Table IV.

TABLE IV

Time required for 50%, (LT50), and 99%, (LT99), lethal and residual effects by contact on various pyrethroids and combinations of pyrethroids and rosemary oil.

| | Rate (% by weight) | LT50 (min) | LT95 (min) | slope |
|---|---|---|---|---|
| Rosemary Oil | 1.0 | 28.61 | 118.03 | 2.08 |
| | 0.50 | 43.98 | 263.88 | 1.64 |
| Permethrin | 0.01 | 20.78 | 490.348 | 0.93 |
| Permethrin/Rosemary Oil | 0.01/0.50 | 26.50 | 157.31 | 1.65 |
| Resmethrin | 0.01 | 31.94 | 417.12 | 1.15 |
| Resmethrin/Rosemary Oil | 0.01/0.50 | 20.14 | 109.72 | 1.74 |
| Tetramethrin | 0.01 | $1.4 \times 10^4$ | $6.5 \times 10^6$ | 0.35 |
| Tetramethrin/Rosemary Oil | 0.01/0.50 | 22.88 | 157.08 | 1.53 |

The data in Table IV demonstrate the definite synergistic and increased residual toxicity of rosemary oil with pyrethroids. This increase in efficacy is unexpected and significant.

Example 5

Efficacy of Imidacloprid in Combination with Essential Oils

For each experimental trial ten adult bed bugs were placed in 60 mm glass petri dishes lids. The test composition is aliquoted (100 μL) into the bottom of the small glass petri dish; filter paper is placed on top of the solution. Control is 100 μL acetate. An elapsed time of 60 s was given to allow the filter paper to absorb the liquid composition. The bed bugs in the petri dish lid were inverted onto the treated surface, confining them inside the dish with the treated area. Morbidity, moribund, and mortality was recorded at 5 minute intervals for 2 hours.

Figure 5:
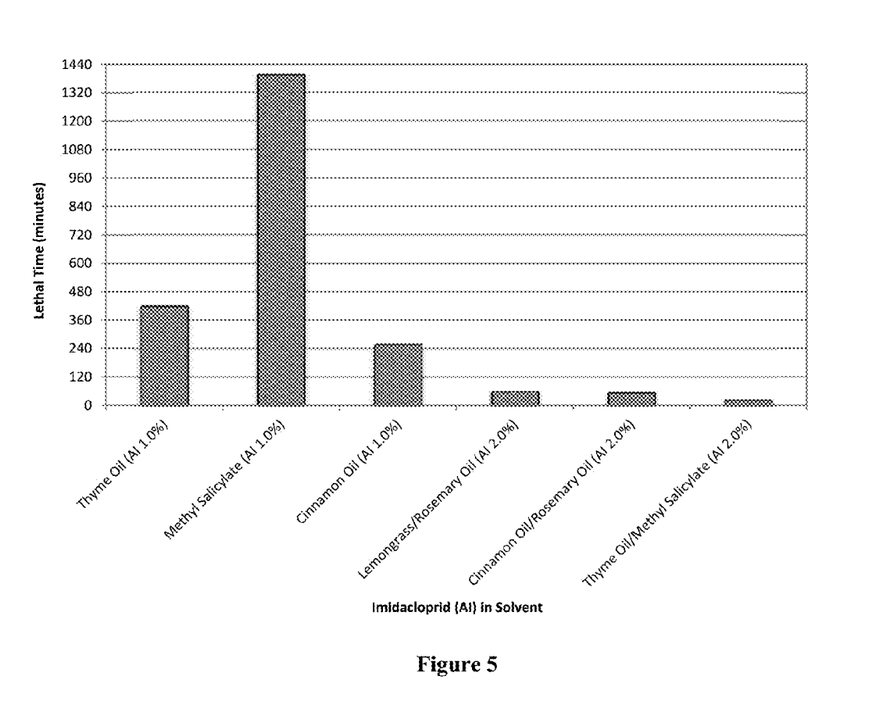
FIG. 5 is 99% lethal time data for imidacloprid in combination with an essential oil and mixtures of essential oils.

The 99% lethal time (LT) for compositions comprising 1% by weight imidacloprid (AI) and thyme oil, methyl salicylate or cinnamon oil and for compositions comprising 2% imidacloprid in a 1:1 mixture of: lemongrass oil and rosemary oil, cinnamon oil and rosemary oil; or thyme oil and methylsalicilate is provided in FIG. 5.

Example 6

Determining the Contact and Residual Efficacy of Aerosol Application of Combinations of Imidacloprid, and/or Methyl Salicylate, and Thyme Oil on Cimex Lectularius Two chambers were used in the following experiment. Chamber one was a polypropylene container with a 114 L capacity, and chamber two was an insulated room with three window panels. The treatment area was 16 m³. The compositions of the present invention were tested against bed bug insecticidal activity in the following manner.

Compositions and individual components of the compositions were prepared that provided the appropriate rates of application for combinations of acetamiprid, chlorfenapyr, and rosemary oil, as well as acetamiprid, chlorfenapyr, and rosemary oil paired and alone. The compositions were aliquoted into an aerosol generation device which is attached to an air compressor and flow meter to regulate the aerosol output. Two sets of fifteen adult bed bugs were used in each experimental run in the 114 L chamber. The bed bugs were placed into 100 mm glass Pyrex dishes lined with filter paper and sealed with a mesh lid to prevent escapes. Each petri dish was set on opposite side of the chamber. For the 16 m$^3$ chamber, fifteen adult bed bugs for each of the six treatment locations plus the control were placed into 100 mm glass Pyrex dishes lined with filter paper. A mesh lid was placed over the Pyrex dish to prevent escapes. The bed bugs were placed in six separate locations throughout the chamber; namely, ground height in corner of north wall, 3 ft height in center of north wall, 5 ft height in corner of west wall, ground height in center west wall, 6 ft height in center of south wall, 3 ft height in corner of south wall. Doors of chamber were on the east wall. Bed bug refuges used in the experimental design cover mesh lid leaving 1 to 2 mm gap opening. Fans were used to circulate the air within the chamber. Aerosol particle sizes were measured using a multi-channel laser aerosol particle sizer. The aerosol particles were binned into 64 channels spanning a size range of 0.2 µm to 10.5 µm. A 100:1 aerosol dilution system was equipped to the particle sizer. Samples of chamber air were taken in 25.5 cm$^3$ volumes every 60 seconds for the duration of each experiment.

Bed bug morbidity, moribundity (knockdown) and mortality was observed and recorded when they are removed from the treated chamber. Observation of bed bug health was continued until all treated bed bugs have died or control mortality has reached 10%.

Figure 6:
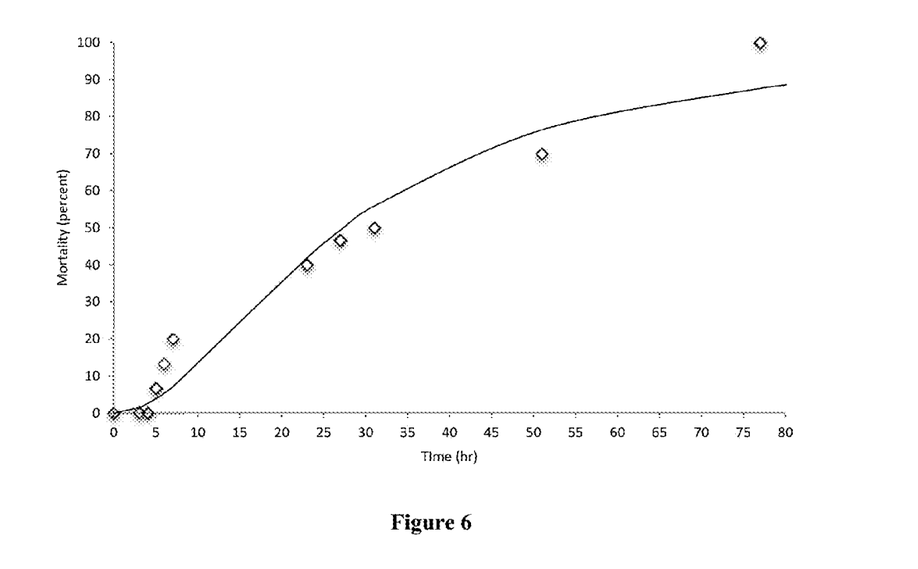
FIG. 6 is kill time data for imidacloprid in combination with thyme oil and methyl salicylate in a small chamber.

FIG. 6 shows the kill time for compositions comprising 2.9% by weight imidacloprid (AI) and thyme oil, methyl salicylate in the 114 L chamber. Aerosol output of composition was 8.18 g/hr.

Figure 7:
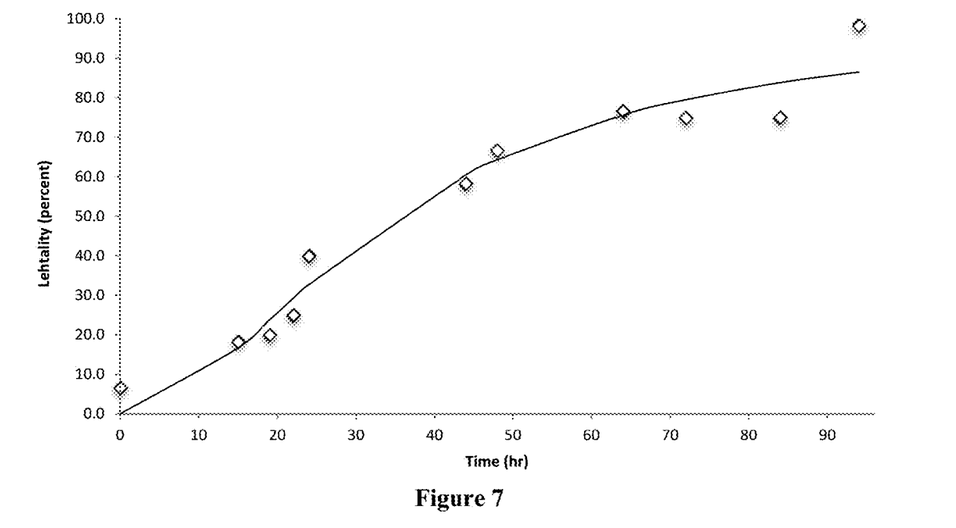
FIG. 7 is lethal time data for imidacloprid in combination with thyme oil and methyl salicylate in a large chamber.

FIG. 7 shows the lethal time (LT) for compositions comprising 2.9% by weight imidacloprid (AI) and thyme oil, methyl salicylate in a 16 m$^3$ chamber. Aerosol output of composition was 63.8 g/hr.

Figure 8:
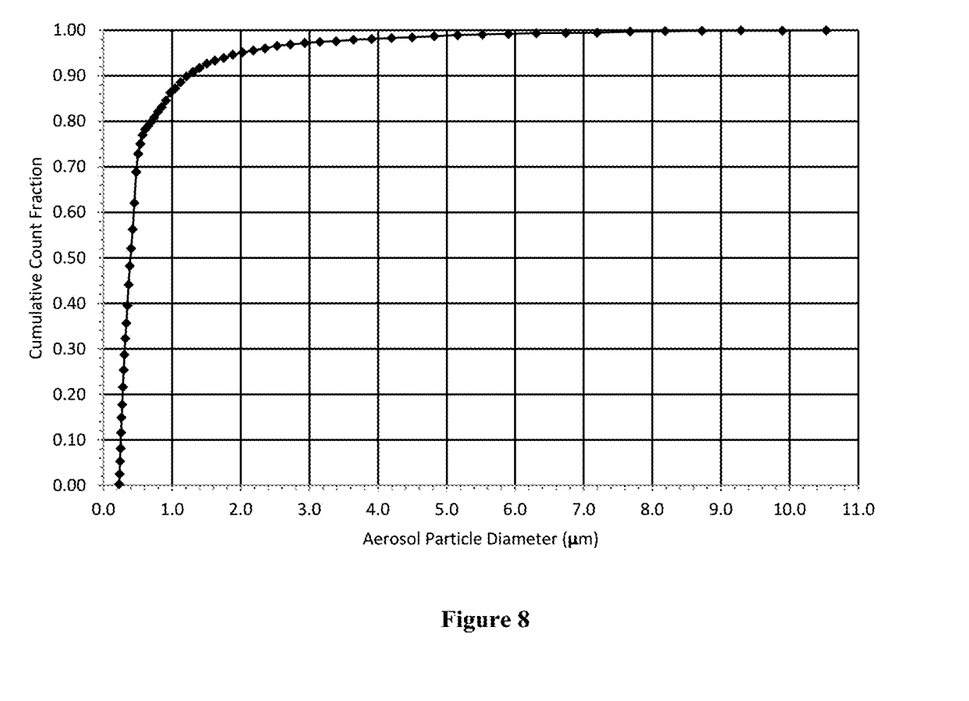
FIG. 8 is shows the cumulative count distribution of aerosolized particles at the aerosol delivery point inside chamber one of Example 6.

FIG. 8 shows the cumulative count distribution of aerosolized particles at the aerosol delivery point inside chamber one: 90% of the total aerosol particles were less than 1.3±0.5 µm in diameter when aerosolized.

Figure 9:
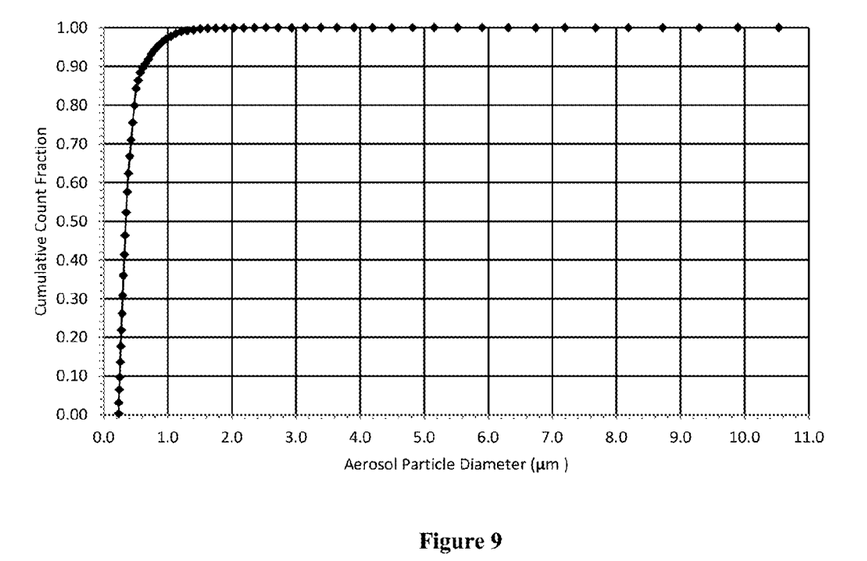
FIG. 9 shows the cumulative count distribution of aerosolized particles present in the air headspace of chamber one of Example 6.

FIG. 9 shows the cumulative count distribution of aerosolized particles present in the air headspace of chamber one: 90% of the total aerosol particles are less than 0.7±0.2 µm in diameter when aerosolized.

Figure 10:
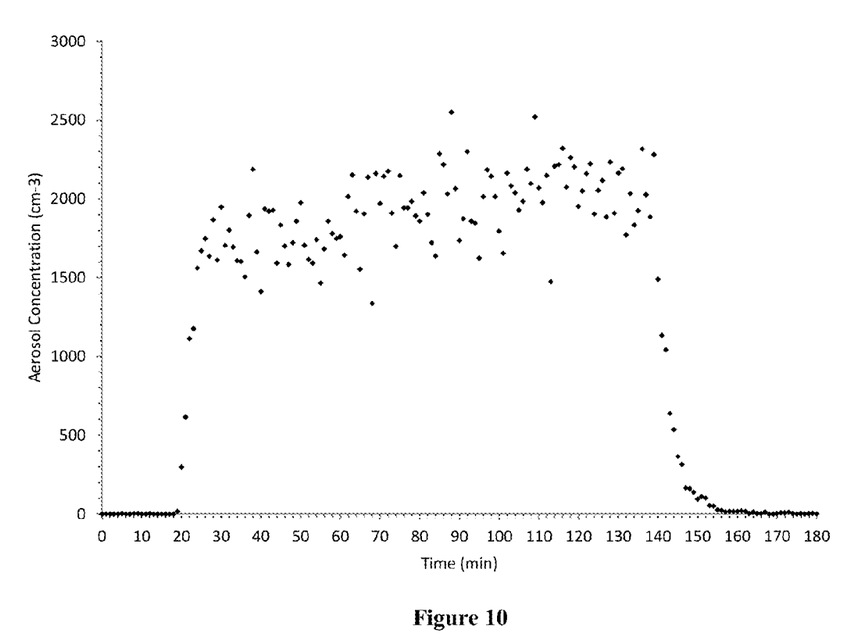
FIG. 10 shows the aerosol number concentration ($cm^{-3}$) present in chamber two of Example 6 during a two hour aerosol treatment.

FIG. 10 shows the aerosol number concentration (cm$^{-3}$) present in chamber two during a two hour aerosol treatment. The aerosol number concentration value ranges from 100 counts/cm$^3$ to 45,000 counts/cm$^3$ or an aerosol mass concentration value ranging from 0.01 mg/m3 to 10 mg/m3.

Figure 11:
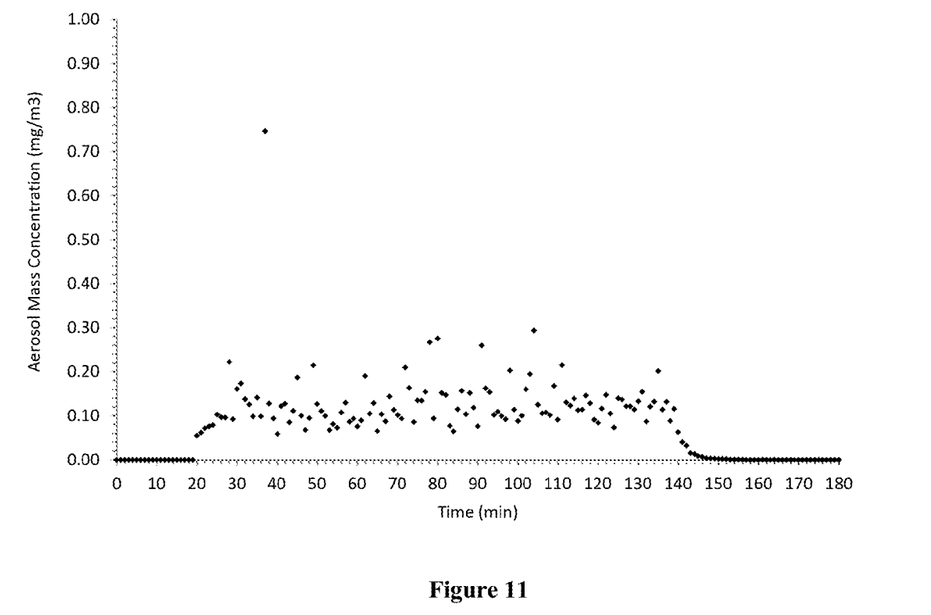
FIG. 11 shows the aerosol mass concentration ($mg/m^3$) present in chamber two of Example 6 during a two hour aerosol treatment.

FIG. 11 shows the aerosol mass concentration (mg/m$^3$) present in chamber two during a two hour aerosol treatment.

This experiment demonstrates that the aerosol application of a liquid composition comprised of a solid insecticide dissolved in a solvent comprising essential oils will knockdown and control pyrethroid-resist bed bugs. The aerosol delivery method produces small particles of insecticide of less than 2 µm, capable of penetrating bed bug harborages in both small and large scale chamber environments causing over 95% lethality to target pest. The aerosol particle size and aerosol concentration have been determined in order to effectively knockdown, control, and cause mortality to target pest.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A liquid composition for controlling a target pest by aerosol application to a space in need thereof, the composition comprising a solid insecticide dissolved in a solvent comprising an essential oil,
wherein:
the solid insecticide is selected from the group consisting of acetamiprid, chlorfenapyr, permethrin, resmethrin, tetramethrin and imidacloprid;
the essential oil is selected from the group consisting of rosemary oil, thyme oil, methyl salicylate, cinnamon oil and lemon grass oil; and
the solid insecticide is present at a concentration of at least 0.01% by weight of the composition.

2. The composition of claim 1, wherein the solid insecticide is present at a concentration of at least 0.1% by weight of the composition.

3. The composition of claim 1, wherein the solid insecticide is present at a concentration of at least 1% by weight of the composition.

4. The composition of claim 1, wherein the solid insecticide is present at a concentration of at least 2% by weight of the composition.

5. The composition of claim 1, wherein the solid insecticide is present at a concentration of at least 3% by weight of the composition.

6. The composition of claim 1, where the insecticide is selected from the group consisting of resmerthrin, tetramethrin, and permethrin.

7. The composition of claim 1, wherein the insecticide is selected from the group consisting of acetamiprid, and imidacloprid.

8. The composition of claim 7, wherein the insecticide is imidacloprid.

9. The composition of claim 7, wherein the insecticide is acetamiprid.

10. The composition of claim 1, wherein the insecticide is chlorofenapyr.

11. The composition of claim 1, wherein the essential oil is selected from the group consisting of methyl salicylate, rosemary oil and thyme oil.

12. The composition of claim 11, wherein the rosemary oil comprises a major constituent selected from the group consisting of α-pinene, 1,8-cineole (eucalyptol), camphene, camphor, β-pinene, β-myrcene, and borneol.

13. The composition of claim 11, wherein the rosemary oil comprises one or more minor constituent selected from the group consisting of bornyl acetate, linalool, β-caryophyllene, limonene, sabinene, verbenone, verbenene, verbenol, 3-octanone, β-phellanderene, terpinene-4-ol, α-terpineol, p-cymene, and γ-terpinene.

14. The composition of claim 11, wherein the thyme oil comprises a major constituent selected from the group consisting of thymol, camphor, ρ-cymene, γ-terpinene and caravacrol.

15. The composition of claim 11, wherein the thyme oil comprises one or more minor constituent selected from the group consisting of myrcene, α-pinene, camphene, borneol, β-caryophyllene, 1,3-octadiene, 1,7-acadiene, 2,4-dymethyl-2,4-heptadiene, sabinene, p-menthene-1, p-menthene-3, α-phellandrene, α-terpinene, limonene, (Z)-β-ocimene, (E)-β-ocimene, α-terpinolene, metha-3,8-diene, p-cymene, trans-dihydrocarvone, thymol methyl ether, carvacrol acetate, β-caryophyllene, calamenene, γ-cadinene, β-pinene and linalool.

16. The composition of claim 1, wherein the essential oil comprises a constituent selected from α-pinene, β-pinene, pulegone, anisole, eucalyptol, eugenol, geraniol, geranyl acetate, linalyl acetate, methyl anthranilate, myrcene, thymol and cymene.

17. The composition of claim 1, further comprising a synergist selected from the group consisting of piperonyl butoxide, isopropyl myistate and phenethyl propionate.

18. The composition of claim 1, comprising at least two essential oils.

19. The composition of claim 18, wherein each essential oil is present in the composition in an amount ranging from 1% to 99% by weight.

20. The composition of claim 18, wherein each essential oil is present in the composition in an amount ranging from 40% to 60% by weight.

21. The composition of claim 1, comprising thyme oil in an amount ranging from 40% to 90% by weight of the composition.

22. The composition of claim 1, comprising methyl salicylate in an amount ranging from 10% to 60% by weight of the composition.

23. The composition of claim 1, wherein the essential oil comprises rosemary oil, and the solid insecticide comprises acetamiprid or chlorfenapyr or both.

24. The composition of claim 18, wherein the essential oils are methyl salicylate and thyme oil, and the solid insecticide is imidacloprid.

25. The composition of claim 1, wherein the target pest is selected from the group consisting of bed bugs (*Cimex* spp), fleas (Siphonoptera), lice (Phthiraptera), silverfish (Zygentoma), crickets (Orthoptera), cockroaches (Blattodea: Blaberoidea), ants, wasps, and bees (Hymenoptera: Fomiciadae, Vespidae, and Apoidea), and flies (Diptera).

26. The composition of claim 25, wherein the target pest is a bed bug (*Cimex* spp).

27. The composition of claim 25, wherein the bed bug is a pyrethroid-resistant bed bug (*Cimex lecturalius*).

* * * * *